US011880987B2

(12) United States Patent
Nakagomi

(10) Patent No.: US 11,880,987 B2
(45) Date of Patent: Jan. 23, 2024

(54) IMAGE PROCESSING APPARATUS, IMAGE PROCESSING METHOD, AND STORAGE MEDIUM

(71) Applicant: CANON KABUSHIKI KAISHA, Tokyo (JP)

(72) Inventor: Keita Nakagomi, Tochigi (JP)

(73) Assignee: Canon Kabushiki Kaisha, Tokyo (JP)

(*) Notice: Subject to any disclaimer, the term of this patent is extended or adjusted under 35 U.S.C. 154(b) by 258 days.

(21) Appl. No.: 17/344,748

(22) Filed: Jun. 10, 2021

(65) Prior Publication Data

US 2021/0304425 A1 Sep. 30, 2021

Related U.S. Application Data

(63) Continuation of application No. PCT/JP2019/049333, filed on Dec. 17, 2019.

(30) Foreign Application Priority Data

Dec. 26, 2018 (JP) .................. 2018-243767

(51) Int. Cl.
*G06T 7/50* (2017.01)
*G06T 7/33* (2017.01)
(Continued)

(52) U.S. Cl.
CPC .............. *G06T 7/33* (2017.01); *G06T 7/337* (2017.01); *G06T 7/50* (2017.01); *G06V 10/25* (2022.01);
(Continued)

(58) Field of Classification Search
CPC ...................................................... G06T 7/33
See application file for complete search history.

(56) References Cited

U.S. PATENT DOCUMENTS

2011/0069063 A1  3/2011  Liao
2013/0259342 A1* 10/2013  Bruder .................. G06T 7/0012
382/131

(Continued)

FOREIGN PATENT DOCUMENTS

CN 103914814 A 7/2014
JP H08103439 A 4/1996

(Continued)

OTHER PUBLICATIONS

Borgefors, Gunilla, Hierarchical Chamfer Matching: A parametric Edge Matching Algorithm, IEEE transactions on pattern analysis and machine intelligence, Nov. 1988, vol. 10, No. 6, pp. 849-865.

(Continued)

*Primary Examiner* — Oneal R Mistry
(74) *Attorney, Agent, or Firm* — Canon U.S.A., Inc. IP Division

(57) ABSTRACT

An image processing apparatus includes a generation unit configured to generate a first distance image having a pixel value based on a distance from an outline of a region that indicates a predetermined part of the subject and is extracted from a first image, and having a resolution lower than a resolution of the first image, and generate a second distance image having a pixel value based on a distance from an outline of a region that indicates the predetermined part and is extracted from a second image, and having a resolution lower than a resolution of the second image, a first calculation unit configured to calculate first deformation information by registering the first distance image and the second distance image, and a second calculation unit configured to calculate second deformation information by registering the first image and the second image based on the first deformation information.

20 Claims, 3 Drawing Sheets

(51) Int. Cl.
    *G06V 10/25* (2022.01)
    *G06V 20/64* (2022.01)

(52) U.S. Cl.
    CPC .... *G06V 20/64* (2022.01); *G06T 2207/10028* (2013.01); *G06T 2207/30008* (2013.01); *G06T 2207/30016* (2013.01); *G06T 2207/30056* (2013.01); *G06T 2207/30061* (2013.01)

(56) References Cited

U.S. PATENT DOCUMENTS

2019/0000318 A1* 1/2019 Caluser ................ A61B 5/0073
2019/0197723 A1* 6/2019 Tanaka ..................... A61B 8/14

FOREIGN PATENT DOCUMENTS

| JP | 2006508746 A | 3/2006 |
| JP | 2007061617 A | 3/2007 |
| JP | 2014054476 A | 3/2014 |
| JP | 2015096196 A | 5/2015 |

OTHER PUBLICATIONS

Min Chen, et al. "Distance Transforms in Multi Channel MR Image Registration" Proc. SPIE Int Soc Opt Eng. Mar. 11, 2011:2011 (7962):79621D.

* cited by examiner

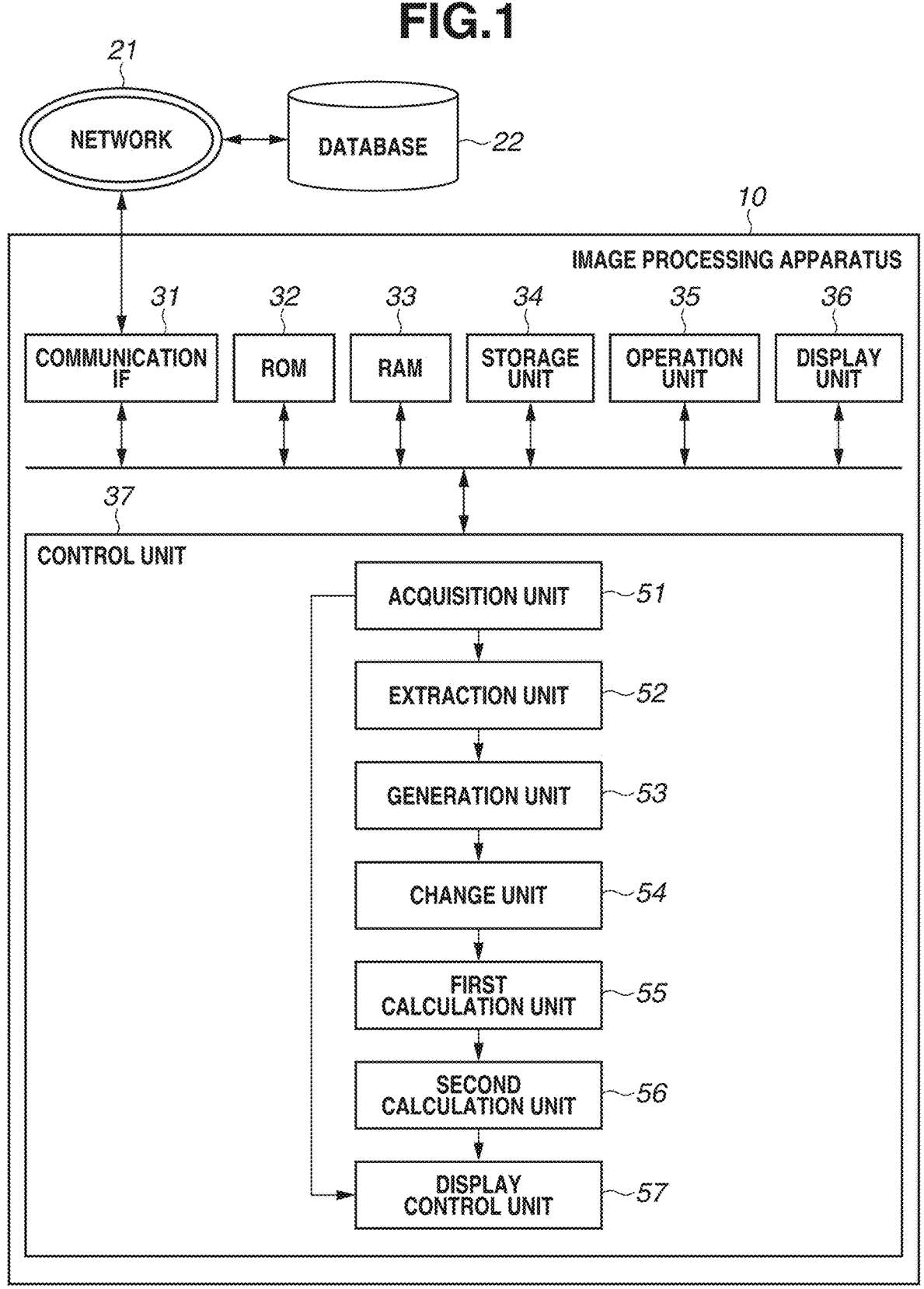

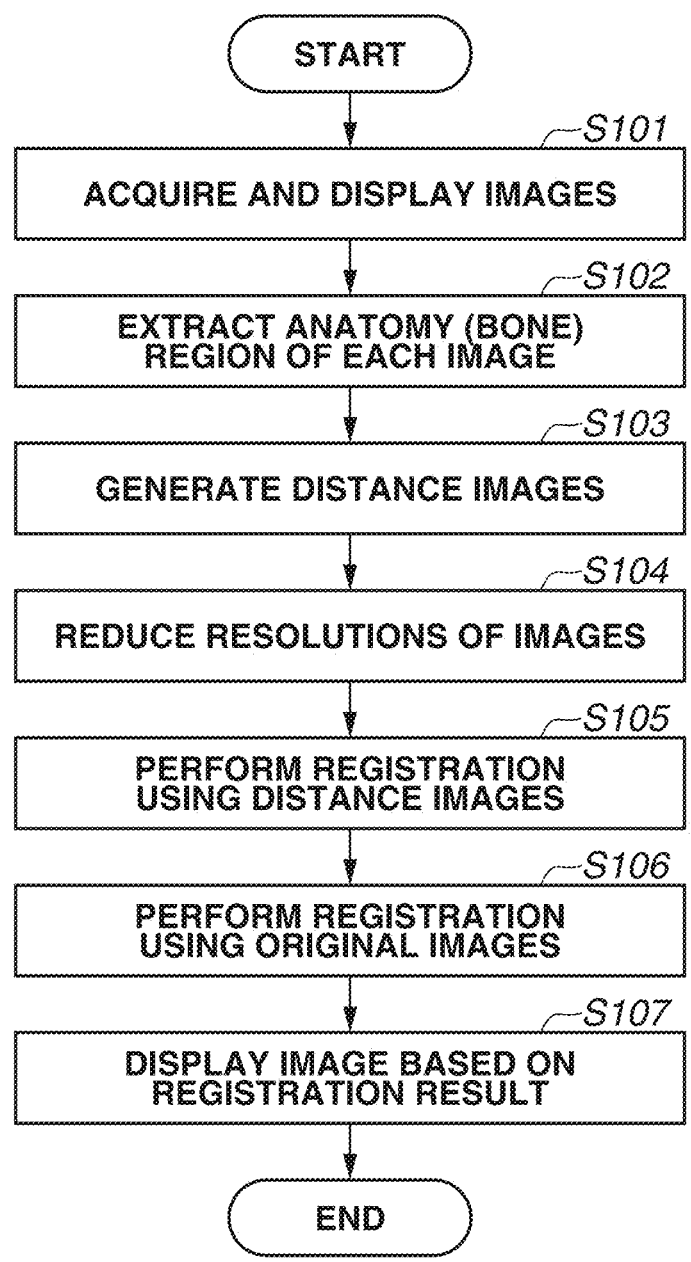

EXAMPLE OF IMAGE REFLECTING
RESULT OF BONE REGION EXTRACTION

EXAMPLE OF DISTANCE IMAGE OF
BONE REGION EXTRACTION RESULT

IMAGE PROCESSING APPARATUS, IMAGE PROCESSING METHOD, AND STORAGE MEDIUM

CROSS-REFERENCE TO RELATED APPLICATIONS

This application is a Continuation of International Patent Application No. PCT/JP2019/049333, filed Dec. 17, 2019, which claims the benefit of Japanese Patent Application No. 2018-243767, filed Dec. 26, 2018, both of which are hereby incorporated by reference herein in their entirety.

BACKGROUND OF THE INVENTION

Field of the Invention

The present invention relates to an image processing apparatus, an image processing method, and a storage medium.

Background Art

In the medical field, a subtraction technique for acquiring an image expressing a temporal change between images as a difference (hereinafter "difference image") is known as a technique to be used in comparing two original images captured at different times (hereinafter "reference image" and "comparative image").

To generate a difference image in which a temporal change of an imaging target is appropriately captured in the subtraction technique, it may be desirable to accurately perform registration processing of associating each pixel of a reference image with that of a comparative image, as preprocessing thereof.

NPL 1 discusses a method of increasing processing accuracy by utilizing an original image and a result of performing processing of extracting a specific region in an image in registration processing. In this technique, an image (hereinafter "distance image") representing the distance from the outline of the extracted region is calculated, and the original image and the distance image are simultaneously used in the registration processing, thus increasing the registration accuracy.

In the technique discussed in NPL 1, however, because two types of image, i.e., the original image and the distance image based on a result of extracting a predetermined part, are simultaneously used in the registration processing, there is such an issue that the calculation cost involved in the processing is high.

CITATION LIST

Non Patent Literature

NPL1: Min Chen, et. al. "Distance Transforms in Multi Channel MR Image Registration" Proc. SPIE Int Soc Opt Eng. 2011 Mar. 11:2011 (7962):79621D.

SUMMARY OF THE INVENTION

The present disclosure is directed to registering two images captured at different times, with higher accuracy, at lower calculation cost.

The present disclosure can also be directed to producing an effect that is derived by each configuration in an embodiment to be described below and that cannot be obtained by a conventional technique.

An image processing apparatus includes an acquisition unit configured to acquire a first image and a second image of a subject that are captured at different times, a generation unit configured to generate a first distance image having a pixel value based on a distance from an outline of a region that indicates a predetermined part of the subject and is extracted from the first image, and having a resolution lower than a resolution of the first image, and generate a second distance image having a pixel value based on a distance from an outline of a region that indicates the predetermined part and is extracted from the second image, and having a resolution lower than a resolution of the second image, a first calculation unit configured to calculate first deformation information by registering the first distance image and the second distance image, and a second calculation unit configured to calculate second deformation information by registering the first image and the second image based on the first deformation information.

Further features of the present invention will become apparent from the following description of exemplary embodiments with reference to the attached drawings.

BRIEF DESCRIPTION OF THE DRAWINGS

FIG. 1 is a functional block diagram illustrating an image processing apparatus according to a first exemplary embodiment.

FIG. 2 is a flowchart illustrating an example of a processing procedure of the image processing apparatus.

DESCRIPTION OF THE EMBODIMENTS

Figure 3A:
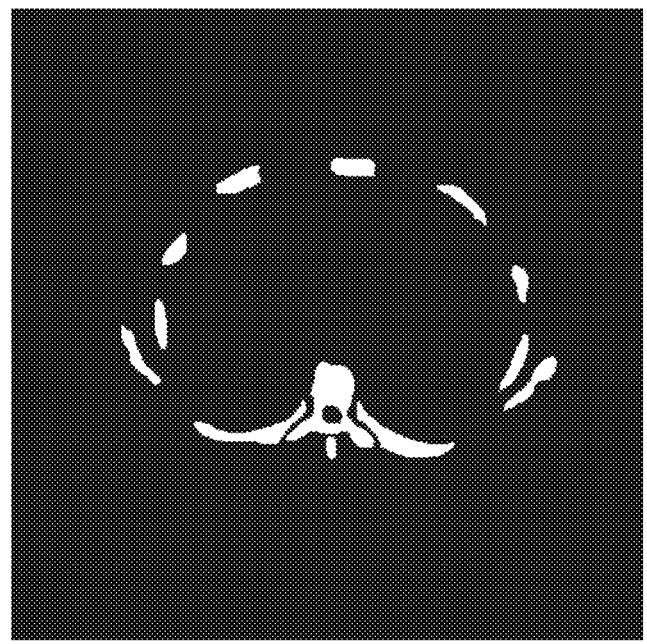
FIG. 3A is a diagram illustrating an example of an image generated by the image processing apparatus.

An exemplary embodiment of an image processing apparatus of the present disclosure will be described in detail below with reference to the drawings.

Components described in this exemplary embodiment are only examples, and the technical scope of the image processing apparatus of the present disclosure is defined by the scope of claims and is not limited by the following individual exemplary embodiments.

First Exemplary Embodiment

An image processing apparatus according to a first exemplary embodiment is an apparatus that displays a plurality of three-dimensional images acquired by various image capturing apparatuses (modalities), such as a computed tomography (CT) apparatus. The image processing apparatus according to the present exemplary embodiment has a registration function of calculating corresponding positions between images, in order to display two-dimensional tomographic images corresponding to two three-dimensional images captured at different times, and a difference image generated from the two two-dimensional tomographic images. Further, the image processing apparatus according to the present exemplary embodiment is characterized by using a distance image calculated from a result of extracting a predetermined anatomy region, together with the original image, in multi-resolution registration processing, in the process of determining the corresponding positions.

In the present exemplary embodiment, an example of performing the registration processing for a bone part included in an image captured by a CT apparatus will be described. An effect of the present exemplary embodiment can be obtained by performing similar processing, also in a case where images obtained by other modalities are registered, or other anatomies are registered.

A configuration and processing of the image processing apparatus of the present exemplary embodiment will be described below with reference to FIG. 1.

FIG. 1 is a block diagram illustrating a configuration example of an image processing system (hereinafter may also be referred to as "medical image processing system") including the image processing apparatus of the present exemplary embodiment. The image processing system includes an image processing apparatus 10, a network 21, and a database 22, as the functional configurations thereof. The image processing apparatus 10 is communicably connected to the database 22 via the network 21. The network 21 includes, for example, a local area network (LAN) and a wide area network (WAN).

The database 22 holds an image of a subject and information associated with the image, and manages the image and the information. The image processing apparatus 10 can acquire the image held in the database 22, via the network 21. The image processing apparatus 10 includes a communication interface (IF) 31 (a communication unit), a read only memory (ROM) 32, a random access memory (RAM) 33, a storage unit 34, an operation unit 35, a display unit 36, and a control unit 37.

The communication IF 31 (the communication unit) includes a LAN card and implements communication between an external device (e.g., the database 22) and the image processing apparatus 10. The ROM 32 includes a nonvolatile memory and stores various programs. The RAM 33 includes a volatile memory and temporarily stores various types of information as data. The storage unit 34 includes a hard disk drive (HDD) and stores various types of information as data. The operation unit 35 includes a keyboard, a mouse, and a touch panel, and inputs an instruction from a user (e.g., a doctor) to various apparatuses.

The display unit 36 includes a display and displays various types of information to the user. The control unit 37 includes a central processing unit (CPU) and controls processing in the image processing apparatus 10. The control unit 37 includes an acquisition unit 51, an extraction unit 52, a generation unit 53, a change unit 54, a first calculation unit 55, a second calculation unit 56, and a display control unit 57, as the functional configurations thereof.

The acquisition unit 51 acquires a reference image and a comparative image to be a registration processing target from the database 22. In other words, the acquisition unit 51 corresponds to an example of an acquisition unit that acquires a first image and a second image of a subject that are captured at different times. In the present exemplary embodiment, an image captured prior to the reference image is used as the comparative image. These images are three-dimensional images of a subject that are acquired by any of various modalities. In the present exemplary embodiment, the image will be described to be a CT image as an example, but may be other types of image. In other words, any three-dimensional or two-dimensional images are applicable to the two images that are the reference image and the comparative image, irrespective of the type of the image, and any images may be used if the image is a target for comparison. In other words, the two images may be images of the same subject, or may be images of different persons, e.g., an image of a healthy person and an image of a patient. Images of different modalities may be used.

The extraction unit 52 extracts a region indicating a predetermined part of the subject from each of the reference image and the comparative image acquired by the acquisition unit 51.

The generation unit 53 calculates a distance value based on the extracted region, for the region indicating the predetermined part of the subject extracted by the extraction unit 52 from each of the reference image and the comparative image, and generates a first distance image and a second distance image. To be more specific, for example, a pixel value based on a distance value representing a distance from the outline of the extracted region is calculated in each of the pixels in the two images by using information about the region extracted by the extraction unit 52, and the first distance image and the second distance image are generated. In other words, the generation unit 53 generates, from the first image, the first distance image having the pixel value based on the distance from the outline of the region extracted in the first image. The generation unit 53 also generates, from the second image, the second distance image having the pixel value based on the distance from the outline of the region extracted in the second image.

The change unit 54 changes an input image to an image having a resolution set beforehand. In the present exemplary embodiment, processing of reducing the resolution is performed on each of the first distance image and the second distance image.

The first calculation unit 55 calculates first image deformation information as information indicating the corresponding positions in the reference image and the comparative image, based on the first distance image and the second distance image generated by the generation unit 53, or on the image generated by the change unit 54. In other words, first deformation information is calculated by registering the first distance image and the second distance image.

The second calculation unit 56 calculates second image deformation information as information indicating the corresponding positions in the reference image and the comparative image, based on the reference image and the comparative image acquired by the acquisition unit 51, and the first image deformation information calculated by the first calculation unit 55. In other words, the second calculation unit 56 calculates the second deformation information by registering the first image and the second image, based on the first deformation information.

In other words, the registration processing in the present exemplary embodiment is performed in multiple stages (multiple resolutions), based on the distance images reduced in resolution and the original images (the reference image and the comparative image). The basic concept of the registration processing in the present exemplary embodiment is based on a concept called coarse-to-fine. In this concept, rough registration processing is performed first, and the result thereof is used in the next registration processing to perform detailed registration. In other words, highly accurate registration is performed by adopting a form of connecting a plurality of types of registration processing in stages.

In step S105 illustrated in a flowchart in FIG. 2 to be described below, to first perform the overall rough registration, the first image deformation information is calculated as image deformation information in the first stage, using the distance images of the low resolutions. In step S106, to perform more detailed registration as registration processing in the second stage, the registration processing is performed using the reference image and the comparative image having the resolutions higher than those of the distance images used in the processing in the first stage, and the second image deformation information is calculated.

The display control unit 57 displays at least two or more images among the input images in an image display area of the display unit 36, based on a result of calculation performed by the second calculation unit 56, in a display form that enables easy comparison between the corresponding positions. For example, the display unit 36 displays, in addition to the reference image and the comparative image, at least one of a deformation image obtained by deforming the comparative image based on the first deformation information or the second deformation information, and a difference image indicating the difference between the reference image and the deformation image.

Each of the components of the image processing apparatus 10 described above functions based on a computer program. For example, the control unit 37 (CPU) reads a computer program stored in the ROM 32 or the storage unit 34 into the RAM 33 used as a work area, and executes the read computer program, so that the function of each of the components is implemented. Some or all of the functions of the components of the image processing apparatus 10 may be implemented using a dedicated circuit. Some of the functions of the components of the control unit 37 may be implemented using a cloud computer.

For example, the functions of the components of the image processing apparatus 10 or the control unit 37 may be implemented by communicably connecting a computing device in a place different from the location of the image processing apparatus 10 to the image processing apparatus 10 via the network 21 to exchange data between the image processing apparatus 10 and the computing device.

Next, an example of processing of the image processing apparatus 10 in FIG. 1 will be described with reference to FIG. 2.

FIG. 2 is a flowchart illustrating an example of a processing procedure of the image processing apparatus 10. In the present exemplary embodiment, performing registration based on an anatomical feature of a bone part will be described as an example, but the present exemplary embodiment is also applicable to a case where other part is set.

(Step S101: Acquisition and Display of Images)

In step S101, in response to a user providing an instruction to acquire an image via the operation unit 35, the acquisition unit 51 acquires a reference image and a comparative image designated by the user from the database 22 and stores the acquired images into the RAM 33. In other words, step S101 corresponds to an example of an image acquisition process of acquiring a first image and a second image of a subject that are captured at different times. At this time, the display control unit 57 may display the images acquired from the database 22 in the image display area of the display unit 36.

(Step S102: Extraction of Anatomy (Bone Part) Region of Each Image)

In step S102, the extraction unit 52 extracts a region (an anatomy region) indicating a predetermined part of the subject, from each of the reference image and the comparative image acquired by the acquisition unit 51. In the present exemplary embodiment, the region indicating the predetermined part of the subject represents a region indicating a bone part that is a registration target. The region indicating the bone part may be subdivided and extracted as, for example, a rib, sternum, or pelvis. In this case, the bone region can be further subdivided and extracted using, for example, a method of acquiring a feature amount representing continuity of pixel values, as discussed in, for example, Japanese Patent Application Laid-Open No. 2017-192691. The region indicating the predetermined part of the subject is not limited to the above-described examples, and may be, for example, an organ such as a liver, lung field, or brain. For example, known techniques including various organ region extraction techniques using threshold processing and graph cuts may be used for this region extraction.

For example, in a case where a region indicating a bone part is extracted from a CT image, if the image is a non-contrast inspection image, the region can be roughly extracted by extracting pixel values greater than or equal to a certain threshold (e.g., 150 [H.U.]) by utilizing such a feature that the pixel values of the bone region are greater than the pixel values of other regions on the image. In other words, the region indicating a predetermined part of the subject is extracted by extracting pixel values greater than or equal to a predetermined threshold.

Afterwards, graphic form shaping may be performed using a morphology operation, such as hole filling processing or closing processing to fill a missing portion in the extracted region. Not only the pixel value of the original image but also a value representing a known feature amount that can be calculated from the original image may be used in this extraction processing. In a case where region data to be a registration target is prepared beforehand, the image may be read in here. The above-described processing after the region extraction may not be performed.

In the present exemplary embodiment, a predefined pixel value, such as a pixel value=255, is to be stored in pixels (foreground pixels/graphic pixels) corresponding to the extracted region, and also a predefined pixel value, such as a pixel value=0, is to be stored in pixels (background pixels) corresponding to a region that is not extracted.

In other words, in the image representing the region indicating the predetermined part of the subject extracted in this step S102, a fixed value is stored in each of the inside and outside of the extracted region, and thus the distribution of the pixel values of each of the regions becomes uniform. In other words, the region indicating the predetermined part of the subject is extracted by storing binary pixel values different from each other in the pixels inside the extracted region and in the pixels outside the extracted region. The predetermined pixel value to be stored in each of the inside and outside of the extracted region is not limited to the above-described example, and a pixel value different from the predetermined pixel value may be stored in part of each of the inside and outside of the extracted region.

Upon completion of the image processing relating to the region extraction, the extraction unit 52 stores the result of extracting the region indicating the predetermined part of the subject and an image reflecting the result of the region extraction as illustrated in FIG. 3A into the RAM 33, for each of the reference image and the comparative image.

(Step S103: Generation of Distance Images)

Figure 3B:
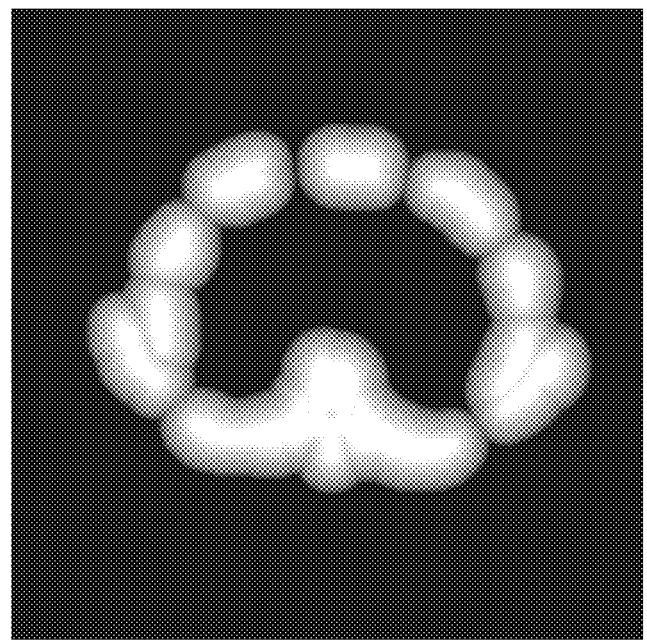
FIG. 3B is a diagram illustrating an example of an image generated by the image processing apparatus.

In step S103, the generation unit 53 calculates a distance value representing a distance from the outline of the region in each pixel, based on information about the region extracted in step S102 in each of the reference image and the comparative image. Subsequently, the generation unit 53 generates a first distance image and a second distance image based on the calculated distance values, and stores the generated images into the RAM 33. In other words, the first distance image having a pixel value based on the distance from the outline of the region extracted in the first image is generated from the first image. The second distance image having a pixel value based on the distance from the outline of the region extracted in the second image is generated from the second image. This calculation is performed on the image reflecting the extraction result with respect to each of the reference image and the comparative image, and a known technique such as distance conversion processing for an extracted region may be used. Referring to FIGS. 3A and 3B, processing such as the distance conversion processing is performed on the image having been subjected to the region extraction in binary as illustrated in FIG. 3A, and the distance image illustrated in FIG. 3B is generated.

In the present exemplary embodiment, a Euclidean distance from the outline of the extracted region is calculated in each pixel of the image, but other distance indexes, such as a Manhattan distance, may be used. The reciprocal of the distance value representing the distance from the outline or known value conversion such as sigmoid transformation may be used to increase a value near the outline of a graphic pixel. Further, a signed distance for distinguishing between the inside (the foregoing/graphic region, pixel value=255) and the outside (the background, pixel value=0) of the extracted region may be calculated assigning a plus or minus sign to the distance value, or a distance with no sign may be used.

The distance image (FIG. 3B) generated through the above-described processing is characterized by having different density values for the inside (the foreground) and the outside (the background) of the extracted region, as compared with the image (FIG. 3A) reflecting the result of the region extraction generated in step S102.

Specifically, FIG. 3B illustrates a multivalued image, whereas FIG. 3A illustrates a binary image. For example, the distance image illustrated in FIG. 3B has such a pixel value in a pixel in the extracted region that the longer the Euclidean distance from the outline of the extracted region is, the larger the pixel value is. The pixels whose Euclidean distances from the outline of the extracted region are more than or equal to a predetermined value may be converted to uniformly have almost the same pixel values, by performing known value conversion such as the sigmoid transformation on the pixels in the inside of the extracted region.

Alternatively, in the distance image, a first pixel value may be stored in a pixel included in a first range of the Euclidean distance from the outline of the extracted region, and a second pixel value greater than the first pixel value may be stored in a pixel included in a second range in which the Euclidean distance is longer than that of the first range, in the pixels in the extracted region.

In the distance image, a pixel in the outside of the extracted region has such a pixel value that the longer the Euclidean distance from the outline of the extracted region is, the smaller the pixel value is. The pixels whose Euclidean distances from the outline of the extracted region are more than or equal to a predetermined value may be converted to uniformly have almost the same pixel values, by performing known value conversion such as the sigmoid transformation on the pixels in the outside of the extracted region.

Alternatively, a first pixel value may be stored in a pixel included in a first range of the Euclidean distance from the outline of the extracted region, and a second pixel value greater than the first pixel value may be stored in a pixel included in a second range of the Euclidean distance longer than that of the first range, in at least some of the pixels in the outside of the extracted region. The above-described method of converting the density value is merely an example and the conversion is not limited to this example.

The above-described light and shade expression produces the effect of increasing a capture range for misregistration in the registration processing. In other words, the use of the distance image in the registration processing can address larger misregistration, and thus the registration accuracy can be expected to be improved also in a case where the initial misregistration is large.

In the present exemplary embodiment, the distance image based on the distance value representing the distance from the outline of the region extracted in step S102 is used, but a distance that can be calculated based on other places, such as an image based on a distance from the center of gravity of this region, may be used. Alternatively, the distance image may be generated based on one or more feature points identified by a known technique of extracting a feature point from an image, using a known feature amount, such as scale-invariant feature transform (SIFT). In this process, the image used in calculating the feature point may be the image reflecting the result of the region extraction by the extraction unit 52, or may be the original image (each of the reference image and the comparative image) acquired by the acquisition unit 51. In a case where the feature point is directly calculated from the original image acquired by the acquisition unit 51, the region extraction processing in step S102 described above may be omitted.

(Step S104: Reduction of Resolutions of Images)

In step S104, the change unit 54 performs resolution reduction processing on the first distance image and the second distance image generated by the generation unit 53, generates images smaller in size than the input images, and stores the generated images into the RAM 33.

In the present exemplary embodiment, the resolution reduction processing is performed on the distance image of each of the reference image and the comparative image, but this processing may be performed after step S101 or step S102, and may be performed a plurality of times in stages depending on individual processing. In other words, there may be adopted a flow of reducing the resolution of each of the reference image and the comparative image and extracting the predetermined part of the subject from the image having the reduced resolution.

In other words, the order of step S102 to S104 is not limited to the above-described example. Any order may be adopted if the first distance image having the pixel value based on the distance from the outline of the region indicating the predetermined part of the subject extracted in the first image and having the resolution lower than that of the first image is generated, and if the second distance image having the pixel value based on the distance from the outline of the region extracted in the second image and having the resolution lower than that of the second image is generated.

It is desirable to adaptively determine the order of the step for the region extraction and the step for the image resolution reduction, in consideration of a balance with the accuracy of the region extraction processing for extracting the anatomy to be the registration target.

For example, in a case where a small structure, such as a rib or sternum, is to be extracted, the region extraction processing may become difficult if the resolution is excessively reduced before the region extraction processing, and thus it is desirable to adopt a flow of changing the resolution of the distance image.

In contrast, in a case where a relatively large structure, such as a lung field, liver, or pelvis, is to be extracted, the region can be relatively easily extracted from the image even if the resolution of the image is low, and thus the resolution of the image may be reduced before the extraction processing. This can remove a small noise. The calculation cost of the region extraction processing and the distance calculation processing in the subsequent stages can be reduced, so that an increase in the processing speed can be expected.

Alternatively, in step S102, predetermined information (e.g., part information such as the organ name of a registration target) may be received as input information, and the processing may be performed in a step order determined beforehand for each piece of the predetermined information. For example, in a case where a pelvis is designated as a registration target organ, the anatomy region extraction and the distance image generation are performed after the resolution reduction. In a case where a rib is designated as a registration target organ, the resolution reduction processing is performed after the anatomy region extraction and the distance image generation. In other words, step S102 corresponds to an example of a process of acquiring information about a predetermined part of a subject. This enables automatic switching to an appropriate processing procedure based on predetermined information provided as an input.

(Step S105: Registration Using Distance Images)

In step S105, the first calculation unit 55 performs the registration processing on the reference image and the comparative image, based on the first distance image and the second distance image each having the low resolution and generated in step S104. In other words, for each pixel of the first distance image having the low resolution, the corresponding position in the second distance image having the low resolution is calculated as the first image deformation information. Here, the first image deformation information is, for example, information for the same resolution as that of the first distance image having the low resolution, and can be generated as a displacement field image holding a displacement vector (to the corresponding pixel of the second distance image having the low resolution) in each pixel of the first distance image having the low resolution. In a case where the image resolution reduction processing in step S104 is performed before the distance image generation processing in step S103, the output image of step S103 is the distance image having the low resolution, and thus this output image can be used.

The first calculation unit 55 stores the first image deformation information and an image (a first deformation image) generated such that the comparative image matches the reference image based on the first image deformation information into the RAM 33. This first deformation image is not necessarily generated, and it is sufficient if the first image deformation information is output and stored. Alternatively, it is sufficient if processing using the first image deformation information as an input is performed and the result thereof is output to the second calculation unit 56.

Of the multi-stage registration performed in the present exemplary embodiment, the registration processing in the first stage performed in step S105 uses the distance image having the low resolution for the following reason. The purpose of this registration processing in the first stage is a rough registration as described above, and thus a high-resolution image having detailed information is not suitable for the processing.

This is because, in the initial stage before the registration, the positions of two images are often greatly shifted, and in such a case, information representing match or mismatch in value for each pixel of a high-resolution image can become a noise in the registration processing. In other words, a risk of falling into a local solution in the registration processing increases. The use of a low-resolution image has such an effect that rough image information is preferentially used, and thus the use of the low-resolution image in the initial stage of the registration processing is advantageous.

Further, the use of an image with a reduced resolution reduces the number of pixels of a processing target, and thus a reduction in the calculation cost can also be expected. These advantages are similar to those of general multi-resolution registration using an image pyramid.

Next, in the present exemplary embodiment, in order to address a case where a registration error is large in the initial state, the distance images are used in place of the original image such as the reference image and the comparative image, in performing the registration processing with the low resolution. The distance image that can be calculated from a result of extracting the region indicating the predetermined part of the subject is used, so that processing dedicated to the region indicating the predetermined part of the subject can be implemented in calculating approximate corresponding positions.

For example, in a case where bone parts are registered, bone-region registration can be more preferentially performed by using the distance image of a result of extracting a bone region, instead of using the original image in which an organ other than bone appears. The reason for using the distance image here instead of directly using the image resulting from the extraction is that the distance image can address a larger initial registration error.

This processing of registration between the two distance images (the distance image of the reference image and the distance image of the comparative image) may be executed by using a linear registration technique, such as affine transformation, or a nonlinear registration technique, such as free form deformation (FFD) and large deformation diffeomorphic metric mapping (LDDMM), or may be executed by the combination of these techniques.

Further, those types of registration processing or the combination of those types of registration processing may be repeated a plurality of times. This registration processing itself using the distance images in step S105 may be performed within a multi-resolution frame.

(Step S106: Registration Using Original Images)

In step S106, the second image deformation information is calculated by registering the reference image and the comparative image, based on the first image deformation information. Specifically, after the first image deformation information is calculated, the second calculation unit 56 performs the registration processing using the original images having the resolutions higher than those of the images used in the processing in the first stage, by using the first image deformation information as the initial value, thus obtaining the second image deformation information that is deformation information further detailed than the first image deformation information. In other words, for each pixel of the reference image, the corresponding position in the comparative image is calculated as the second image deformation information. Here, the second image deformation information is, for example, information about the same resolution as that of the reference image, and can be generated as a displacement field image holding a displacement vector (to the corresponding pixel of the comparative image) in each pixel of the reference image. For this detailed registration processing as well, the above-described known registration techniques can be used, and a method different from the method of calculating the first image deformation information may be used. As a method other than the method of comparing the comparative image and the reference image as the original images, the registration may be performed using an image having been subjected to preprocessing, such as noise removal and edge enhancement, on each of the images. In a case where the reference image and the comparative image are images obtained by different modalities, for example, various techniques for registration between different modalities using mutual information amount may be used. The first image deformation information is calculated using a low-resolution image, and thus the resolution of the first deformation information may be matched the resolution of the image to be used for the processing in the second stage, when necessary for the registration technique to be used in the registration processing in the second stage.

Here, the distance image with the high resolution is not used for the registration in step S106 because it is conceivable that the distance image has the following disadvantage. By nature of the registration based on the distance image and the result of extracting the region indicating the predetermined part of the subject, the accuracy of this registration largely depends on the accuracy of the region extraction processing. This does not become an issue in a case where the accuracy of the region extraction processing is sufficiently high and the processing is robust, but this can become an issue in the detailed registration processing in a case where there is a missed part or excessive pickup in a result of the region extraction processing.

For example, in a case where a region representing a small structure of a certain anatomy is missed in the region extraction processing, this region is not treated as a registration processing target, and thus there arises such an issue that the registration cannot be performed on the region that has been missed in the extraction processing. In general, when considering an issue in extraction of a certain anatomy, having difficulty in automatically extracting a fine structure is conceivable.

Thus, in a case where the accuracy of the region extraction processing is insufficient with respect to the accuracy desirable for the registration processing, it is conceivable that it is desirable to use an original image with a large amount of information in the detailed registration stage. For these reasons, it is apparent that, in a case where the rough registration processing and the detailed registration processing are combined, the overall processing performance can be enhanced by selecting the most appropriate image in each stage. In the present exemplary embodiment, the distance image representing the distance from the outline of the bone part is used to perform the rough registration, and the original image with a larger amount of information is used in performing the detailed registration, so that the registration processing with high accuracy is implemented.

The registration processing in this step may use the method discussed in NPL 1, instead of using only the original images. In this case as well, the misregistration for the registration target is reduced through the processing in step S105, and thus the effect of reducing the calculation cost before obtaining a final registration result is maintained.

Finally, the second calculation unit 56 stores the second image deformation information and an image (a deformation image) generated by performing image deformation to adjust the comparative image to the reference image based on the second image deformation information into the RAM 33. This deformation image is not necessarily generated, and it is sufficient if the second image deformation information is output and stored. Alternatively, it is sufficient if processing using the second image deformation information as an input is performed and the result thereof is output. In an example, the result of calculating the difference between the reference image and the deformation image may be output. A region of interest (ROI) on the reference image corresponding to a ROI on the comparative image may be derived based on the above-described second deformation information. Alternatively, there may be adopted such a configuration that a slice of the second image substantially corresponding to each slice of the first image is identified based on the above-described second deformation information, and the correlation information thereof is output.

(Step S107: Display of Image Based on Registration Result)

In step S107, the display control unit 57 displays the deformation image in the image display area, together with the reference image and the comparative image that are the input images. In this process, an image representing the difference between the two images, i.e., a difference image (e.g., an image obtained by subtracting the deformation image from the reference image), may be calculated and displayed in the image display area.

According to the present exemplary embodiment, the distance image with the low resolution and the original image with the high resolution are both used in the multi-resolution registration processing, so that there is the effect of providing the user with a result of registering the two images captured at different times, with higher accuracy, at lower calculation cost.

According to the present exemplary embodiment, the distance image, which is more suitable for the rough registration than the original image, and the original image are combined and used in the frame of the multi-resolution registration processing, thus providing a result of a high accuracy registration to the user.

(Modification)

In the above-described exemplary embodiment, a description has been provided of the example in which the distance images with lower resolutions than those of the original images are generated before the first calculation unit 55 performs the processing of calculating the first deformation information in the processing in step S105, and the generated distance images are used in the registration processing. However, the procedure before calculating the deformation information for performing a rough registration at low calculation cost is not necessarily limited to this example. For example, the deformation information may be calculated using a method by which an equivalent effect can be obtained in the registration processing in step S105, instead of changing the resolution before the registration processing. To be more specific, there may be used a method of reducing processing target pixels by sampling at least one (e.g., the first distance image) of the images and referring to the sampled image, in comparing the first distance image and the second distance image, which are processing targets, in the registration processing in step S105. For example, when the first deformation information is calculated, the first distance image may be sampled to have a resolution lower than that of the original image and then referred to, and the corresponding positions of the first distance image and the second distance image may be calculated with respect to a position (pixel) obtained by sampling. In this process, the resolution of the first deformation information is the same as that of the first distance image. In other words, the resolution of the first deformation information is lower than the resolution of the above-described second deformation information, and thus the effect of providing the user with the result of performing the registration with higher accuracy at lower calculation cost can be maintained, as with the first exemplary embodiment.

Other Exemplary Embodiments

The technology of the disclosure can take any of forms including a system, an apparatus, a method, and a program or recording medium (storage medium), for example. Specifically, the technology may be applied to a system composed of a plurality of devices (e.g., a host computer, an interface device, an imaging apparatus, and a web application) and may be applied to an apparatus composed of a single device.

It goes without saying that the object of the present invention is accomplished as follows. First, a recording medium (or storage medium) storing a program code (a computer program) of software implementing the functions of the exemplary embodiment described above is supplied to a system or apparatus. Needless to say, the storage medium is a computer-readable storage medium. A computer (or a CPU, or a micro processing unit (MPU)) of the system or apparatus reads out the program code stored in the recording medium and executes the read-out program code. In this case, the program code itself read out from the recording medium implements the functions of the exemplary embodiment described above, and the recording medium storing the program code forms the present invention.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the present disclosure, two images captured at different times can be registered with higher accuracy, at lower calculation cost.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:
1. An image processing apparatus comprising:
a memory storing a program; and
one or more processors which, by executing the program, function as:
an acquisition unit configured to acquire a first image and a second image of a subject that are captured at different times;
a generation unit configured to generate a first distance image having a pixel value based on a distance from an outline of a region that indicates a predetermined part of the subject and is extracted from the first image, and having a resolution lower than a resolution of the first image, and generate a second distance image having a pixel value based on a distance from an outline of a region that indicates the predetermined part and is extracted from the second image, and having a resolution lower than a resolution of the second image;
a first calculation unit configured to calculate first deformation information through first registration processing of registering the first distance image and the second distance image; and
a second calculation unit configured to calculate second deformation information through second registration processing of registering the first image and the second image based on the first deformation information.

2. An image processing apparatus comprising:
a memory storing a program; and
one or more processors which, by executing the program, function as:
an acquisition unit configured to acquire a first image and a second image of a subject that are captured at different times;
a generation unit configured to generate a first distance image having a pixel value based on a distance from an outline of a region that indicates a predetermined part of the subject and is extracted from the first image, and generate a second distance image having a pixel value based on a distance from an outline of a region that indicates the predetermined part and is extracted from the second image;
a first calculation unit configured to calculate first deformation information through first registration processing of registering the first distance image and the second distance image; and
a second calculation unit configured to calculate second deformation information through second registration processing of registering the first image and the second image based on the first deformation information,
wherein a resolution of the first deformation information is lower than a resolution of the second deformation information.

3. The image processing apparatus according to claim 1, wherein the first calculation unit and the second calculation unit calculate the first deformation information and the second deformation information, respectively, by deforming one of the first image and the second image with respect to the other, the one being captured prior to the other.

4. The image processing apparatus according to claim 1, wherein the generation unit extracts the region indicating the predetermined part by extracting a pixel value greater than or equal to a predetermined threshold.

5. The image processing apparatus according to claim 1, wherein the generation unit extracts the region indicating the predetermined part by storing binary pixel values different from each other in a pixel inside the region indicating the predetermined part and a pixel outside the region indicating the predetermined part.

6. The image processing apparatus according to claim 1, wherein the generation unit generates the first distance image and the second distance image having a pixel value based on a Euclidean distance from the outline of the region indicating the predetermined part.

7. The image processing apparatus according to claim 6, wherein the generation unit generates the first distance image and the second distance image in which pixel values of at least some of pixels inside the region indicating the predetermined part are greater as the Euclidean distance is longer.

8. The image processing apparatus according to claim 6, wherein the generation unit generates the distance image in which pixels at the Euclidean distance greater than or equal to a predetermined value inside the region indicating the predetermined part uniformly have same pixel values.

9. The image processing apparatus according to claim 6, wherein the generation unit generates the distance image in which pixel values of at least some of pixels outside the region indicating the predetermined part are smaller as the Euclidean distance is longer.

10. The image processing apparatus according to claim 9, wherein the generation unit generates the distance image in which pixels having the Euclidean distance greater than or equal to a predetermined value outside the region indicating the predetermined part uniformly have same pixel values.

11. The image processing apparatus according to claim 1, wherein the second calculation unit calculates the second deformation information using the first deformation information as an initial value.

12. The image processing apparatus according to claim 1, further comprising a display control unit configured to display, on a display unit, at least one of a deformation image and a difference image, the deformation image being obtained by deforming the second image based on the first deformation information or the second deformation information, the difference image indicating a difference between the first image and the deformation image.

13. The image processing apparatus according to claim 1, wherein the predetermined part is at least one of a bone part, a liver, a lung field, and a brain.

14. An image processing method comprising:
acquiring a first image and a second image of a subject that are captured at different times;
generating a first distance image having a pixel value based on a distance from an outline of a region that indicates a predetermined part of the subject and is extracted from the first image, and having a resolution lower than a resolution of the first image, and generating a second distance image having a pixel value based on a distance from an outline of a region that indicates the predetermined part and is extracted from the second image, and having a resolution lower than a resolution of the second image;
calculating, as first calculation, first deformation information through first registration processing of registering the first distance image and the second distance image; and
calculating, as second calculation, second deformation information through second registration processing of registering the first image and the second image based on the first deformation information.

15. The image processing method according to claim 14, wherein, in the generating, the first distance image is generated by reducing the resolution after an image having the pixel value based on the distance from the outline of the region is generated in the first image, and the second distance image is generated by reducing the resolution after an image having the pixel value based on the distance from the outline of the region is generated in the second image.

16. The image processing method according to claim 14, wherein, in the generating, the region is extracted after the resolution of the first image is reduced, and the first distance image having the pixel value based on the distance from the outline of the region is generated in the first image, and the region is extracted after the resolution of the second image is reduced, and the second distance image having the pixel value based on the distance from the outline of the region is generated in the second image.

17. The image processing method according to claim 14, further comprising acquiring information about the predetermined part of the subject,
wherein, in the generating, in a case where the predetermined part of the subject of the acquired information is a rib or a sternum, the first distance image is generated by reducing the resolution after an image having the pixel value based on the distance from the outline of the region is generated in the first image, and the second distance image is generated by reducing the resolution after an image having the pixel value based on the distance from the outline of the region is generated in the second image.

18. The image processing method according to the claim 17, wherein, in the generating, in a case where the part of the subject of the acquired information is a lung field, a liver, or a pelvis, the first distance image is generated by reducing the resolution before an image having the pixel value based on the distance from the outline of the region is generated in the first image, and the second distance image is generated by reducing the resolution before an image having the pixel value based on the distance from the outline of the region is generated, in the second image.

19. An image processing method of registering a first image and a second image of a subject, the image processing method comprising:
registering, as first registration, a first distance image generated from the first image and having a pixel value based on a distance from an outline of a region indicating a predetermined part of the subject, and a second distance image generated from the second image and having a pixel value based on a distance from an outline of a region indicating the predetermined part of the subject, at a resolution lower than resolutions of the first image and the second image; and
registering, as second registration, the first image and the second image having the resolutions higher than the resolutions of the first distance image and the second distance image, using deformation information acquired through the first registration.

20. A non-transitory computer-readable storage medium storing a program that causes a computer to function as each unit of the image processing apparatus according claim 1.

* * * * *